United States Patent [19]

Adams et al.

[11] Patent Number: 5,660,816

[45] Date of Patent: Aug. 26, 1997

[54] CLEAR HAIR SPRAY FORMULATIONS CONTAINING A LINEAR SULFOPOLYESTER

[75] Inventors: L. Jane Adams, Kingsport; D. Michael Garber, Jonesborough; Sandra N. Porter, Kingsport; Andy H. Singleton, Kingsport; Vicki L. Underwood, Kingsport, all of Tenn.

[73] Assignee: Eastman Chemical Company, Kingsport, Tenn.

[21] Appl. No.: 523,312

[22] Filed: Sep. 5, 1995

Related U.S. Application Data

[63] Continuation of Ser. No. 81,897, Jun. 25, 1993, abandoned.
[51] Int. Cl.$^6$ ........................................ A61K 7/11
[52] U.S. Cl. .................... 424/45; 424/47; 424/70.11; 424/70.15; 424/70.16; 424/DIG. 1; 424/DIG. 2; 514/957; 132/210
[58] Field of Search ........................ 424/70.11, 71, 424/45, DIG. 1, DIG. 2, 78.02, 47; 514/957

[56] References Cited

U.S. PATENT DOCUMENTS

| | | | |
|---|---|---|---|
| 4,300,580 | 11/1981 | O'Neill et al. | 424/70.02 |
| 5,158,762 | 10/1992 | Pierce | 424/71 |

FOREIGN PATENT DOCUMENTS 0551748   7/1993   European Pat. Off. .

OTHER PUBLICATIONS

Oteri, R. et al. (1991). Cosmetics & Toiletries, vol. 106, pp. 29–34.

*Primary Examiner*—Raj Bawa
*Attorney, Agent, or Firm*—John D. Thallemer; Harry J. Gwinnell

[57] ABSTRACT

A clear hair spray formulation which exhibits less than 30 NTU's and contains a linear sulfopolyester and a water-soluble polymer wherein the formulation is in water or a water/alcohol mixture. The sulfopolyester has a glass transition temperature of 40° C. to 60° C. and contains repeat units from the reaction product of a dicarboxylic acid, a diol and a difunctional sulfomonomer. The difunctional sulfomonomer is present in an amount from 18.5 to 22.5 mole percent based on 100 mole percent dicarboxylic acid and 100 mole percent diol. The hair spray formulation may optionally contain a propellant.

12 Claims, No Drawings

CLEAR HAIR SPRAY FORMULATIONS CONTAINING A LINEAR SULFOPOLYESTER

CROSS REFERENCE TO RELATED APPLICATIONS

This application is a continuation of application Ser. No. 08/081,897, filed Jun. 25 1993, which application is now abandoned.

FIELD OF THE INVENTION

This invention relates to hair spray formulations based on (1) a sulfonate-containing, water-dispersible or water-dissipatible, linear polyester having a glass transition temperature of 40° C. to 60° C., In addition, the formulations contain water or a water/alcohol mixture as the liquid vehicle and optionally a propellant. The diol component of the sulfopolyester contains 10 to 30 mole percent 1,4-cyclohexanedimethanol. The sulfopolyester contains 18.5 to 22.5 mole percent sulfomonomer, and the sulfopolyester has a glass transition temperature (Tg) of 40° C. to 60° C. The hair spray formulations may be applied in pump or aerosol form.

BACKGROUND OF THE INVENTION

The use of water-dispersible linear sulfopolyesters in hair spray formulations has been disclosed in U.S. Pat. Nos. 4,300,580 and 5,158,762. U.S. Pat. No. 4,300,580, issued Nov. 17, 1981, and assigned to Eastman Kodak Company, discloses hair grooming formulations containing a sulfopolyester comprising a dicarboxylic acid, a diol wherein at least 20 mole percent is a poly(ethylene glycol), and 8 to 45 mole percent of a dicarboxylic acid sulfomonomer. U.S. Pat. No. 5,158,762, issued Oct. 27, 1992, and assigned to ISP Investments Inc., discloses hair spray compositions containing a blend of two polymers. One of the polymers is a sulfopolyeser comprising a dicarboxylic acid, a diol wherein at least 40 mole percent is 1,4-cyclohexanedimethanol, and 16 to 25 mole percent of a sulfomonomer. U.S. Pat. No. 5,158,762 states that useful sulfopolyesters are AQ 38 and AQ 55 which are available from Eastman Chemical Company. It is interesting to note that while the patent discloses a range of sulfomonomer of 16 to 25 mole percent, AQ 38 has 11 mole percent sulfomonomer. Moreover, AQ 38 has 22 mole percent of 1,4-cyclohexanedimethanol which is below the 40 mole percent requirement set forth in U.S. Pat. No. 5,158,762. In contrast, neither AQ 38 nor AQ 55 are operable in the present invention. The other polymer in U.S. Pat. No. 5,158,762 is a water soluble polymer which includes polyvinyl pyrrolidone (PVP) and polyvinyl acetate.

Such hair grooming compositions generally perform effectively in providing most of the properties considered desirable for hair preparation, including fine spray patterns, prolonged curl retention under humid conditions, good holding power and resistance to build-up. However, these and other hair spray formulations available in the art are generally cloudy and contain precipitate that clogs the exit ports of aerosol cans or pump containers.

The present inventors have unexpectedly discovered four critical ranges that are necessary to produce clear hair spray compositions. The diol component of the sulfopolyester must contain 10 to 30 mole percent 1,4-cyclohexanedimethanol; the sulfopolyester must contain 18.5 to 22.5 mole percent sulfomonomer; the sulfopolyester must have a glass transition temperature (Tg) of 40° C. to 60° C.; and the sulfopolyester must have an inherent viscosity (I.V.) of 0.2 to 0.6 dl/g. The clear hair spray compositions of the present invention exhibit less than 30 NTU's which is a measure of turbidity. In the cosmetic field greater than 30 NTU's is characteristic of a cloudy mixture that is visible to the eye.

SUMMARY OF THE INVENTION

Accordingly, it is one object of the present invention to provide a clear hair spray formulation.

It is another object of the invention to provide a hair spray formulation which is not tacky, has a fast drying rate, acceptable body, consistency and exhibits improved curl retention.

Another object of the invention is to provide a hair spray formulation having excellent storage stability and which does not clog the exit port of an aerosol or pump container.

These and other objects are accomplished herein by a clear hair spray composition comprising:

(1) a sulfopolyester having a Tg of 40° C. to 60° C. consisting essentially of repeat units from
  (a) a dicarboxylic acid selected from the group consisting of aromatic dicarboxylic acids, saturated aliphatic dicarboxylic acids, cycloaliphatic dicarboxylic acids, and combinations thereof;
  (b) a diol provided 10 to 30 mole percent of the diol is 1,4-cyclohexanedimethanol; and
  (c) a difunctional sulfomonomer containing at least one sulfonate group attached to an aromatic nucleus wherein the functional groups are hydroxy, carboxy or amino, provided the difunctional sulfomonomer is present in an amount from 18.5 to 22.5 mole percent based on 100 mole percent dicarboxylic acid and 100 mole percent diol, provided that the hair spray composition contains 1 to 20 weight percent of the sulfopolyester; and (2) a liquid vehicle selected from the group consisting of water and a water/alcohol mixture.

DESCRIPTION OF THE INVENTION

The hair sprays of this invention contain a sulfopolyester, component (1), in an amount of about 1 to about 20 weight percent, preferably less than 10 weight percent, based on the total weight of the hair spray formulation. The sulfopolyesters have an inherent viscosity (I.V.) of 0.2 to 0.6 dl/g as measured at 23° C. using 0.50 grams of polymer per 100 ml of a solvent consisting of 60% by weight phenol and 40% by weight tetrachloroethane. The sulfopolyester has a glass transition temperature of 40° C. to 60° C. and contains repeat units from a dicarboxylic acid, a diol and a difunctional sulfomonomer.

Dicarboxylic acids useful in the present invention include aromatic dicarboxylic acids preferably having 8 to 14 carbon atoms, saturated aliphatic dicarboxylic acids preferably having 4 to 12 carbon atoms, and cycloaliphatic dicarboxylic acids preferably having 8 to 12 carbon atoms. Specific examples of dicarboxylic acids are: terephthalic acid, phthalic acid, isophthalic acid, naphthalene-2,6-dicarboxylic acid, cyclohexanedicarboxylic acid, cyclohexanediacetic acid, diphenyl-4,4-dicarboxylic acid, succinic acid, glutaric acid, adipic acid, azelaic acid, sebacic acid, and the like. The sulfopolyester may be prepared from two or more of the above dicarboxylic acids.

It should be understood that use of the corresponding acid anhydrides, esters, and acid chlorides of these acids is included in the term "dicarboxylic acid".

The diol component of the polyester contains 10 to 30 mole percent of 1,4-cyclohexanedimethanol. In addition to 1,4-cyclohexanedimethanol, suitable diols include cycloaliphatic diols preferably having 6 to 20 carbon atoms or aliphatic diols preferably having 3 to 20 carbon atoms. Examples of such diols to be used with 1,4-cyclohexanedimethanol are: ethylene glycol, diethylene glycol, triethylene glycol, propane-1,3-diol, butane-1,4-diol, pentane-1,5-diol, hexane-1,6-diol, 3-methylpentanediol-(2, 4), 2-methylpentanediol, (1,4), 2,2,4-trimethylpentane-diol-(1,3), 2-ethylhexanediol, (1,3), 2,2-diethylpropane-diol, (1,3), hexanediol-(1,3), 1,4-di-(hydroxyethoxy), benzene, 2,2-bis-(4-hydroxycyclohexyl)-propane, 2,4-dihydroxy, 1,1, 3,3, tetramethyl, cyclobutane, 2,2-bis-(3-hydroxyethoxyphenyl), propane, and 2,2-bis-(4, hydroxypropoxyphenyl)-propane. The polyester may be prepared from two or more of the above diols.

The difunctional sulfomonomer component of the polyester may be a dicarboxylic acid or an ester thereof containing a sulfonate group ($-SO_3^-$), a diol containing a sulfonate group, or a hydroxy acid containing a sulfonate group. The cation of the sulfonate salt may be Na+, Li+, K+, $NH_4+$, and substituted ammonium. The term "substituted ammonium" refers to ammonium substituted with an alkyl or hydroxy alkyl radical having 1 to 4 carbon atoms. The difunctional sulfomonomer contains at least one sulfonate group attached to an aromatic nucleus wherein the functional groups are hydroxy, carboxy or amino.

Advantageous difunctional sulfomonomer components are those wherein the sulfonate salt group is attached to an aromatic acid nucleus such as benzene, naphthalene, diphenyl, oxydiphenyl, sulfonyldiphenyl or methylenediphenyl nucleus. Preferred results are obtained through the use of sulfophthalic acid, sulfoterephthalic acid, sulfoisophthalic acid, 4-sulfonaphthalene-2,7- dicarboxylic acid, and their esters. The sulfomonomer is present in an amount from 18.5 to 22.5 mole percent, based on 100 mole percent dicarboxylic acid and 100 mole percent diol.

It is important to note that all four of the critical ranges must be satisfied in order to attain a clear hair spray composition. The diol component of the sulfopolyester must contain 10 to 30 mole percent 1,4-cyclohexanedimethanol; the sulfopolyester must contain 18.5 to 22.5 mole percent sulfomonomer; the sulfopolyester must have a glass transition temperature of 40° C. to 60° C.; and the sulfopolyester must have an inherent viscosity of 0.2 to 0.6 dl/g. The hair sprays of the present invention exhibit less than 30 NTU's which is a measure of the turbidity of a mixture. In the cosmetic field greater than 30 NTU's is characteristic of a cloudy mixture that is visible to the eye.

Component (2) of the hair spray is a liquid vehicle. The liquid vehicle of the formulations may be water or a water/alcohol mixture. Distilled or deionized water are the preferred sources of water since tap water generally contains ions which may precipitate the sulfopolyester, component (1). The alcohol should have two to four carbon atoms. Specific alcohols include ethanol, isopropanol, and t-butanol.

The liquid vehicle in aerosol hair sprays is preferably water. However, a water/alcohol mixture may be employed as long as the alcohol is present in an amount less than about 55 weight percent. In such aerosol hair spray formulations where an alcohol/water mixture is employed, preferably 35 to 45 weight percent of the mixture is alcohol. In pump formulations, the liquid vehicle is preferably a water/alcohol mixture wherein the alcohol is present in an amount less than about 55 weight percent to satisfy current environmental standards. The preferred alcohol is ethanol. In a pump hair spray formulation containing only a sulfopolyester, component (1) and a liquid vehicle, component (2), the liquid vehicle will be present in an amount of about 80 to about 99 weight percent of the hair spray. However, if additional ingredients are used in the hair spray formulation, the amount of the liquid vehicle will be proportionally reduced. For example, in the case of an aerosol hair spray containing a water soluble polymer and a propellant, the liquid vehicle is preferably present in an amount of 55 to 70 weight percent, based on the total formulation.

The hair spray compositions may optionally contain a water-soluble polymer, component (3), which is prepared from monomers having one or more of the following structures:

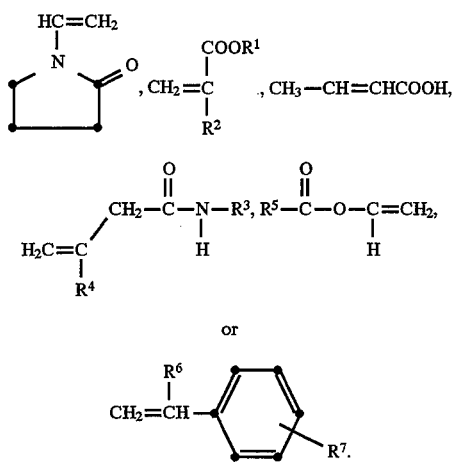

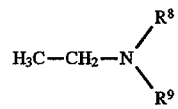

In the above formulas, $R^1$ is a $C_1-C_5$ aliphatic group, preferably a $C_1-C_3$ alkyl group, or is of the structure $$H_3C-CH_2-N\begin{matrix}R^8\\R^9\end{matrix}$$

$R^8$ and $R^9$ are, independently, a $C_1-C_5$ alkyl group. $R^2$ is a $C_1-C_{10}$ aliphatic group, preferably a $C_1-C_3$ alkyl group. $R^3$ is a $C_1-C_{16}$ aliphatic group, preferably a $C_8$ alkyl group, $R^4$ is H or a $C_1-C_8$ aliphatic group, preferably H or a $C_8$ group. $R^5$ is a $C_1-C_8$ aliphatic group, preferably $C_9$ alkyl group, $R^6$ is hydrogen or methyl, and $R^7$ is hydrogen or an alkyl group having 1 to 4 carbon atoms.

Accordingly, suitable water soluble polymers include polyvinyl pyrrolidone (PVP), polyvinyl caprolactam, polyvinyl acetate (VA), polyacrylates and methacrylates, and copolymers and terpolymers of such monomers, such as VP/VA, VA/crotonic acid/vinyl neodecanoate, VA/crotonic acid, or octylacrylamide/acrylates/butyl aminoethyl methacrylate, VA, mono-n-butyl maleate and isobornyl acrylate; and VP/VC/dimethylaminoethyl methacrylate.

A preferred vinyl polymer or copolymer contains at least 50 mole percent of the residues of n-vinyl lactam monomer such as N-vinylpyrrolidinone. A preferred terpolymer is derived from the polymerization of vinyl caprolactam, vinylpyrrolidone and an ammonium derivative monomer having from 6–12 carbon atoms selected from dialkyl dialkenyl ammonium halide and a dialkylamino alkyl acrylate or methacrylate.

The water-soluble polymers may be prepared according to known procedures wherein, for example, a N-vinyl lactam is polymerized, optionally in the presence of one or more other vinyl monomers such as those described above. The N-vinylpyrrolidinone/vinyl acetate copolymers supplied by BASF under the trademark LUVISKOL VA are typical of the water-soluble polymers which may be used in the hair spray formulations of the present invention. The preferred water-soluble polymers comprise homopolymers of N-vinyl-2-pyrrolidinone and copolymers of N-vinyl-2-pyrrolidinone and up to 50 mole percent vinyl acetate having weight average molecular weights in the range of about 1000 to 100,000. The water-soluble polymers are generally present in an amount of about 1 to about 7 weight percent, based on the total weight of the hair spray formulation.

For aerosol hair spray formulations, a propellant, component (4), is necessary. The propellant is selected from the group consisting of a $C_1-C_4$ aliphatic hydrocarbons and dimethyl ether. The aliphatic hydrocarbons may be branched or straight chain and include methane, ethane, propane, n-butane, isobutane, or mixtures thereof. A preferred aliphatic hydrocarbon propellant is a mixture containing about 83 percent isobutane and about 17 percent propane. The propellant is present in an amount of about 3 to about 40 weight percent of the total aerosol hair spray formulation. In the case where a $C_1-C_4$ aliphatic hydrocarbon is used as the propellant, generally about 3 to about 10 weight percent, preferably 4 to 7 weight percent, is employed. In the case where dimethyl ether is used as the propellant, generally, about 30 to about 40 weight percent, preferably, 30 to 35 weight percent, is employed.

Other conventional additives such as preservatives, fragrances, antifoaming agents, hair conditioners, plasticizers, etc. may be added in such quantities as desired, up to about 5.0% by weight of the total formulation. Although the film-forming formulations described herein are particularly useful as aerosol hair sprays for the grooming of hair, it is possible that the formulations, with or without modification, may be used in other types of personal care products.

The materials and testing procedures used for the results shown herein are as follows:

DYMEL A (CTFA Adopted Name: Dimethyl Ether) available from DuPont, is a dimethyl ether and is used as a propellant.

LUVISKOL VA 73W PVP/VA (CTFA Adopted Name: PVP/VA Copolymer), available from BASF, is a water soluble vinyl copolymer of 70 mole percent of N-vinyl-2-pyrrolidinone and 30 mole percent of vinyl acetate (50% solids), and is used as a fixative.

GLYDANT (CTFA Adopted Name: DMDM Hydantoin) available from Lonza, Inc. is 1-(hydroxymethyl)-5,5-dimethyl hydantoin, and is used as a antimicrobial.

SDA-40C is ethanol that has been diluted with ethyl acetate, and is available from Eastman Chemical Company.

Glass transition temperature was determined using a differential scanning calorimeter (DSC).

Inherent viscosity (I.V.) was measured at 23° C. using 0.50 grams of polymer per 100 ml of a solvent consisting of 60% by weight phenol and 40% by weight tetrachloroethane.

Turbidity was measured in NTU's using a model DRT-100B Turbidimeter.

The invention will be further illustrated by a consideration of the following examples, which are intended to be exemplary of the invention. All parts and percentages in the examples are on a weight basis unless otherwise stated.

EXAMPLES I-X (1) Preparation of water-dispersible sulfopolyesters.

A round bottom flask equipped with ground-glass head, an agitator shaft, nitrogen inlet and a side arm was charged with isophthalic acid, 5-sodiosulfoisophthalic acid (SIP), diethylene glycol (DEG), and 1,4-cyclohexanedimethanol (CHDM), in the mole percents as set forth in Table I. In each Example, titanium isopropoxide (50 ppm of titanium), and sodium acetate (10% of the mole% of SIP), were added. The flask was immersed in a Belmont bath at 200° C. for one hour under a nitrogen sweep. The temperature of the bath was increased to 230° C. for one hour. The temperature of the bath was increased to 280° C. and the flask was heated for 45 minutes under reduced pressure of 0.5 to 0.1 mm of Hg. The flask was allowed to cool to room temperature and the copolyester was removed from the flask. The sulfopolyesters were extruded and pelletized. The mole percent of the components for each of the sulfopolyesters, glass transition temperatures and inherent viscosities are listed in Table I.

(2) Preparation of aerosol hair spray formulations using the sulfopolyesters of Examples I-VIII.

Ten grams of each of the sulfopolyesters prepared in Examples I-VIII, were dispersed in 90 grams of distilled water by heating and stirring until a temperature of 75° to 85° C. was reached. After cooling to 40° C. any water lost during heating was replaced. The mixtures were vacuum filtered through a course center glass filter. 1-(hydroxymethyl)-5,5-dimethyl hydantoin, 0.2 grams was added.

To 65 grams of each of the mixtures was added 42 milliliters of dimethyl ether. The mixtures were sprayed into a glass cuvette which was placed in the Turbidimeter. The turbidity results are listed in Table I.

(3) Preparation of pump hair spray formulations using the sulfopolyesters of Examples I-X.

Ten grams of each of the sulfopolyesters prepared in Examples I-X, were dispersed in 90 grams of distilled water by heating and stirring until a temperature of 75° to 85° C. was reached. After cooling to 40° C. any water lost during heating was replaced. The mixtures were vacuum filtered through a course center glass filter. 1-(hydroxymethyl)-5,5-dimethyl hydantoin, 0.2 grams was added.

To 25 grams of each of the mixtures was added 25 grams of SDA 40C. The mixtures were poured into a glass cuvette which was placed in the Turbidimeter. The mole percent of the components of the sulfopolyesters and turbidity results are listed in Table I.

TABLE I

| Example | Diol | (Mole %) | SIP (Mole %) | IV (dl/g) | Tg (°C.) | Turbidity (NTU's) Aerosol | Pump |
|---------|------|----------|--------------|-----------|----------|---------------------------|------|
| I | CHDM<br>DEG | 24.2<br>75.8 | 15.6 | 0.29 | 39 | 41.5 | 30.5 |
| II | CHDM<br>DEG | 21.5<br>78.5 | 19.4 | 0.33 | 41 | 16.5 | 12.7 |
| III | CHDM<br>DEG | 21.9<br>78.1 | 20.2 | 0.33 | 42 | 18.9 | 10.8 |
| IV | CHDM<br>DEG | 23.0<br>77.0 | 22.0 | 0.33 | 47 | 15.7 | 6.4 |
| V | CHDM<br>DEG | 20.7<br>79.3 | 22.6 | 0.19 | 37 | 30.8 | 25.1 |
| VI | CHDM<br>DEG | 21.5<br>78.5 | 11.0 | 0.36 | 38 | 64.6 | 50.4 |
| VII | CHDM<br>DEG | 46.0<br>54.0 | 18.0 | 0.33 | 55 | 36.1 | 60.0 |

TABLE I-continued

| Example | Diol | (Mole %) | SIP (Mole %) | IV (dl/g) | Tg (°C.) | Turbidity (NTU's) Aerosol | Pump |
|---|---|---|---|---|---|---|---|
| VIII | CHDM DEG | 20.6 79.4 | 20.1 | 0.29 | 43 | — | 12.8 |
| IX | CHDM DEG | 36.8 63.2 | 19.8 | 0.18 | 44 | — | 52.3 |
| X | CHDM DEG | 34.0 66.0 | 20.6 | 0.28 | 47 | — | 38.0 |

KEY TO ABBREVIATIONS:
CHDM = 1,4-cyclohexane dimethanol
DEG = diethylene glycol
SIP = 5-sodiosulfoisophthalate The data in Table I indicates that aerosol and pump hair sprays prepared using the critical ranges of the present invention (Examples II–VIII) exhibit less than 30 NTU's which is a measure of the turbidity of a mixture as compared to hair sprays wherein one or more critical limitation is not satisfied. It is important to note that in the cosmetic field greater than 30 NTU's is characteristic of a cloudy mixture that is visible to the eye.

EXAMPLES XI–XVII (1) Preparation of aerosol hair spray formulations using the sulfopolyesters prepared in Examples I–VII.

Ten grams of each of the sulfopolyesters prepared in Examples I–VII, were dispersed in 85 grams of distilled water by heating and stirring until a temperature of 75° to 85° C. was reached. After cooling to 40°C. any water lost during heating was replaced and 5 grams of a water soluble vinyl copolymer consisting of 70 mole percent of N-vinyl-2-pyrrolidinone and 30 mole percent of vinyl acetate (50% solids) was added. The mixtures were vacuum filtered through a course center glass filter. 1-(hydroxymethyl)-5,5-dimethyl hydantoin, 0.2 grams was added.

To 65 grams of each of the mixtures was added 42 milliliters of dimethyl ether. The mixtures were sprayed into a glass cuvette which was placed in the Turbidimeter. The mole percent of the components of the sulfopolyesters and turbidity results are listed in Table II.

(2) Preparation of pump hair spray formulations using the sulfopolyesters prepared in Examples I–VII.

Ten grams of each of the sulfopolyesters prepared in Examples I–VII, were dispersed in 85 grams of distilled water by heating and stirring until a temperature of 75° to 85° C. was reached. After cooling to 40° C. any water lost during heating was replaced and 5 grams of a water soluble vinyl copolymer consisting of 70 mole percent of N-vinyl-2-pyrrolidinone and 30 mole percent of vinyl acetate (50% solids), was added. The mixtures were vacuum filtered through a course center glass filter. 1-(hydroxymethyl)-5,5-dimethyl hydantoin, 0.2 grams was added.

To 25 grams of each of the mixtures was added 25 grams of SDA 40C. The mixtures were poured into a glass cuvette which was placed in the Turbidimeter. The mole percent of the components of the sulfopolyesters and turbidity results are listed in Table II.

TABLE II

| Example | Diol | (Mole %) | SIP (Mole %) | IV (dl/g) | Tg (°C.) | PVP/VA (Wt. %) | Turbidity (NTU's) Aerosol | Pump |
|---|---|---|---|---|---|---|---|---|
| XI | CHDM DEG | 24.2 75.8 | 15.6 | 0.29 | 39 | 5 | 41.0 | 35.8 |
| XII | CHDM DEG | 21.5 78.5 | 19.4 | 0.33 | 41 | 5 | 17.7 | 11.2 |
| XIII | CHDM DEG | 21.9 78.1 | 20.2 | 0.33 | 42 | 5 | 19.8 | 15.0 |
| XIV | CHDM DEG | 23.0 77.0 | 22.0 | 0.33 | 47 | 5 | 15.9 | 8.9 |
| XV | CHDM DEG | 20.7 79.3 | 22.6 | 0.19 | 37 | 5 | 27.8 | 12.4 |
| XVI | CHDM DEG | 21.5 78.5 | 11.0 | 0.36 | 38 | 5 | 63.0 | 54.8 |
| XVII | CHDM DEG | 46.0 54.0 | 18.0 | 0.33 | 55 | 5 | 33.8 | 19.2 |

KEY TO ABBREVIATIONS:
CHDM = 1,4-cyclohexane dimethanol
DEG = diethylene glycol
SIP = 5-sodiosulfoisophthalate The data in Table II indicates that aerosol and pump hair sprays prepared with a water soluble polymer and using the critical ranges of the present invention (Examples XII–XV) exhibit less than 30 NTU's which is a measure of the turbidity of a mixture as compared to hair sprays wherein one or more critical limitation is not satisfied. It is important to note that in the cosmetic field greater than 30 NTU's is characteristic of a cloudy mixture that is visible to the eye.

EXAMPLE XVIII (1) Preparation of a water-dispersible sulfopolyester.

A round bottom flask equipped with ground-glass head, an agitator shaft, nitrogen inlet and a side arm was charged with 78.2 moles of isophthalic acid, 21.8 moles of 5-sodiosulfoisophthalic acid, 83.5 moles of diethylene glycol, and 16.5 moles of 1,4-cyclohexanedimethanol. Titanium isopropoxide (50 ppm of titanium), and sodium acetate (10% of the mole % of SIP), were added. The flask was immersed in a Belmont bath at 200° C. for one hour under a nitrogen sweep. The temperature of the bath was increased to 230° C. for one hour. The temperature of the bath was increased to 280° C. and the flask was heated for 45 minutes under reduced pressure of 0.5 to 0.1 mm of Hg. The flask was allowed to cool to room temperature and the copolyester was removed from the flask. The sulfopolyester was extruded and pelletized. The glass transition temperature and I.V. were determined to be 42° C. and 0.28 dl/g respectively.

(2) Preparation of an aerosol hair spray formulation.

The sulfopolyester prepared above, 7.14 grams, was dispersed in 52.15 grams of distilled water by heating and stirring until a temperature of 75° C. to 85° C. was reached. After cooling to 40° C. any water lost during heating was replaced and 5.71 grams of a water soluble vinyl copolymer consisting of 70 mole percent of N-vinyl-2-pyrrolidinone and 30 mole percent of vinyl acetate (50% solids) was added. The mixture was vacuum filtered through a course center glass filter. 1-(hydroxymethyl)-5,5-dimethyl hydantoin, 0.2 grams was added.

To 65 grams of the mixtures was added 42 milliliters of dimethyl ether. The mixture was sprayed into a glass cuvette which was placed in the Turbidimeter. Turbidity was measured after aging at 45C. for 19 months in an oven. The turbidity was 30.7 NTU's. Thus, the aerosol formulation showed good clarity and storage stability.

EXAMPLE XIX (1) Preparation of a water-dispersible sulfopolyester.

A round bottom flask equipped with ground-glass head, an agitator shaft, nitrogen inlet and a side arm was charged with 73.1 moles of isophthalic acid, 16.9 moles of 5-sodiosulfoisophthalic acid, 81.2 moles of diethylene glycol, and 18.8 moles of 1,4-cyclohexanedimethanol. Titanium isopropoxide (50 ppm of titanium), and sodium acetate (10% of the mole % of SIP), were added. The flask was immersed in a Belmont bath at 200° C. for one hour under a nitrogen sweep. The temperature of the bath was increased to 230° C. for one hour. The temperature of the bath was increased to 280° C. and the flask was heated for 45 minutes under reduced pressure of 0.5 to 0.1 mm of Hg. The flask was allowed to cool to room temperature and the copolyester was removed from the flask. The sulfopolyester was extruded and pelletized. The glass transition temperature and I.V. were determined to be 39° C. and 0.36 dl/g respectively.

(2) Preparation of an aerosol hair spray formulation.

The sulfopolyester prepared above, 7.14 grams, was dispersed in 52.15 grams of distilled water by heating and stirring until a temperature of 75° C. to 85° C. was reached. After cooling to 40° C. any water lost during heating was replaced and 5.71 grams of a water soluble vinyl copolymer consisting of 70 mole percent of N-vinyl-2-pyrrolidinone and 30 mole percent of vinyl acetate (50% solids) was added. The mixture was vacuum filtered through a course center glass filter. 1-(hydroxymethyl)-5,5-dimethyl hydantoin, 0.2 grams was added.

To 65 grams of the mixtures was added 42 milliliters of dimethyl ether. The mixture was sprayed into a glass cuvette which was placed in the Turbidimeter. Turbidity was measured after aging at 45° C. for 19 months in an oven. The turbidity was 53 NTU's. Thus, the aerosol formulation showed good clarity and storage stability.

EXAMPLE XX

Aerosol hair spray formulations were prepared using the sulfopolyesters of Examples IV and VI. The sulfopolyester in Example IV contained 23 mole % CHDM, 22.0 mole % SIP, Tg of 47° C., and an I.V. of 0.33. The sulfopolyester in Example VI contained 21.5 mole % CHDM, 11.0 mole % SIP, Tg of 38° C., and an I.V. of 0.36. Preparation of the aerosol hair sprays is described in Examples I-X.

Testing was done on natural brown, European virgin hair tresses in which about two grams of hair, root end, were glued to a 2" by 2" plastic tab. The tresses were cut so that the length of hair hanging below the tabs was six inches. Prior to applying the hair spray, the tresses had been washed with a nonconditioning shampoo, placed in ethanol bath for 15 minutes, rinsed with deionized water, wrapped around a one inch diameter curler while wet, and placed in an oven at 45° C. to dry. The tresses were removed from the oven and allowed to cool to room temperature.

The aerosol hair spray prepared from the sulfopolyester of Example IV and the aerosol hair spray prepared from the sulfopolyester of Example VI were sprayed on a tress for ten seconds. The tresses were hung in a humidity chamber at 25° C. and 80% relative humidity. The curl loss or droop was determined over a one hour period in ten minute intervals. The test results are listed in Table III.

TABLE III

Curl Retention Evaluation of Aerosol Hair Sprays

| Ex. | Time (minutes) | | | | | | |
| --- | --- | --- | --- | --- | --- | --- | --- |
|  | 0 | 10 | 20 | 30 | 40 | 50 | 60 |
| IV | 100 | 100 | 98.1 | 96.5 | 96.5 | 95.2 | 95.2 |
| VI | 100 | 91.4 | 88.9 | 84.3 | 84.3 | 84.3 | 84.3 |

The test results in Table III indicate that aerosol hair sprays prepared using the critical ranges of the present invention (Example IV) clearly are superior in maintaining curl retention as compared to aerosol hair sprays that fall outside the critical ranges.

EXAMPLE XXI

Pump hair spray formulations were prepared using the sulfopolyesters of Examples IV and VI as described above. The pump hair sprays were sprayed onto tresses as prepared in Example XX.

Each of the pump hair sprays were applied to the tresses by pumping ten times. The tresses were hung in a humidity chamber at 25° C. and 80% relative humidity. The curl loss or droop was determined over a one hour period in ten minute intervals. The test results are listed in Table IV.

TABLE IV

Curl Retention Evaluation of Pump Hair Sprays

| Ex. | Time (minutes) | | | | | | |
| --- | --- | --- | --- | --- | --- | --- | --- |
|  | 0 | 10 | 20 | 30 | 40 | 50 | 60 |
| IV | 100 | 96.3 | 96.3 | 93.5 | 93.5 | 93.5 | 93.5 |
| VI | 100 | 98.1 | 96.2 | 90.4 | 88.5 | 88.5 | 88.5 |

The test results in Table IV indicate that pump hair sprays prepared using the critical ranges (Example IV) of the present invention clearly are superior in maintaining curl retention as compared to pump hair sprays that fall outside the critical ranges.

Many variations will suggest themselves to those skilled in this art in light of the above detailed description. All such obvious modifications are within the full intended scope of the appended claims.

What is claimed is:

1. A clear hair spray formulation exhibiting less than 30 NTU's consisting essentially of the following ingredients:
   (1) 1 to 20 weight percent based on the weight of ingredients (1), (2) and (3) of a linear sulforpolyester having a Tg of 40° C. to 60° C. and inherent viscosity of 0.2 to 0.6 dl/g containing repeat units consisting essentially of the reaction product of a dicarboxylic acid and a diol reacted in a 1:1 mole ratio, wherein the dicarboxylic acid is select from the group consisting of aromatic dicarboxylic acid having 8 to 14 carbon atoms, aliphatic dicarboxylic acids having 4 to 12 carbon atoms, cycloaliphatic dicarboxylic acids having 8 to 12 carbon atoms, and combinations thereof, and the diol is selected from the group consisting of cycloaliphactic diols having 6 to 20 carbon atoms, aliphatic diols having 2 to 20 carbon atoms, and combinations thereof wherein 10 to 30 mole percent of the diol is 1,4-cyclohexanedimethanol, provided 18.5 to 22.5 mole percent of the dicarboxylic acid or diol, based on 100 mole percent dicarboxylic acid and 100 mole percent diol, is a difunctional sulfomonomer which contains at least one sulfonate group attached to an aromatic nucleus wherein the functional groups are hydroxy, carboxy or amino;

(2) 80 to 99 weight percent based on the weight of ingredients (1), (2) and (3) of liquid vehicle selected from the group consisting of water and a water/alcohol mixture provided the amount of alcohol does not exceed 55 weight percent of the water/alcohol mixture; and (3) 1 to 7 weight percent based on the weight of ingredients (1), (2) and (3) of a water-soluble polymer having a weight average molecular weight of $10^3$ to $10^5$, which is prepared from at least one monomer having the following structure:

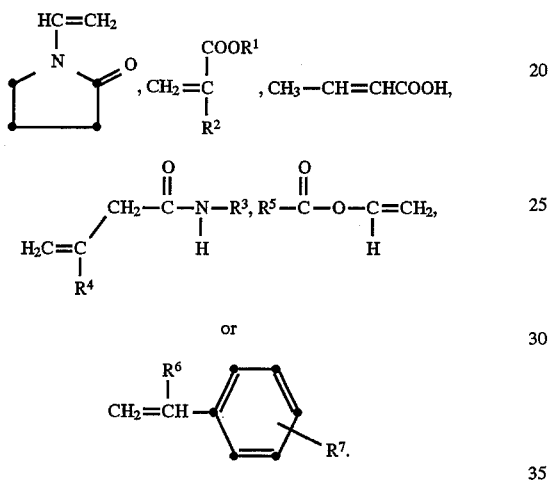

or

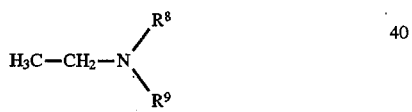

wherein $R^1$ is selected from the group consisting of a $C_1$–$C_5$ aliphatic group and $$H_3C-CH_2-N\overset{R^8}{\underset{R^9}{\diagup\!\!\!\diagdown}}$$

wherein
$R^8$ and $R^9$ are, independently, a $C_1$–$C_5$ alkyl group,
$R^2$ is a $C_1$–$C_{10}$ aliphatic group,
$R^3$ is a $C_1$–$C_{16}$ aliphatic group,
$R^4$ is selected from the group consisting of hydrogen and a $C_1$–$C_8$ aliphatic group,
$R^5$ is a $C_1$–$C_8$ aliphatic group,
$R^6$ is hydrogen or methyl,
$R^7$ is selected from the group consisting of hydrogen and an alkyl group having 1 to 4 carbon atoms.

2. A clear aerosol hair spray formulation exhibiting less than 30 NTU's consisting essentially of the following ingredients:

(1) 1 to 10 weight percent based on the weight of ingredients (1), (2), (3) and (4) of a linear sulfopolyester having a Tg of 40° C. to 60° C. and an inherent viscosity of 0.2 to 0.6 dl/g containing repeat units consisting essentially of the reaction product of a dicarboxylic acid and a diol reacted in a 1:1 mole ratio, wherein the dicarboxylic acid is selected from the group consisting of aromatic dicarboxylic acids having 8 to 14 carbon atoms, aliphatic dicarboxylic acids having 4 to 12 carbon atoms, cycloaliphatic dicarboxylic acids having 8 to 12 carbon atoms, and combinations thereof, and the diol is selected from the group consisting of cycloaliphatic diols having 6 to 20 carbon atoms, aliphatic diols having 2 to 20 carbon atoms, and combinations hereof wherein 10 to 30 mole percent of the diol is 1,4-cyclohexanedimethanol, provided 18.5 to 22.5 mole percent of the dicarboxylic acid or diol, based on 100 mole percent dicarboxylic acid and 100 mole percent diol, is a difunctional sulfomonomer which contains at least one sulfonate group attached to an aromatic nucleus wherein the functional groups are hydroxy, carboxy or amino;

(2) 55 to 70 weight percent based on the weight of ingredients (1), (2), (3) and (4) of a liquid vehicle selected from the group consisting of water and a water/alcohol mixture provided the mount of alcohol does not exceed 55 weight percent of the water/alcohol mixture;

(3) 1 to 7 weight percent based on the weight of ingredients (1), (2), (3) and (4) of a water-soluble polymer having a weight average molecular weight of $10^3$ to $10^5$, which is prepared from at least one monomer having the following structure:

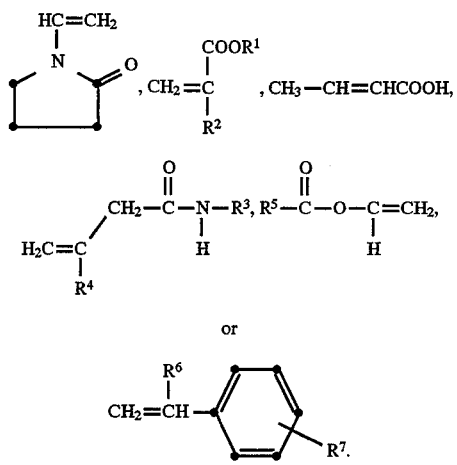

or

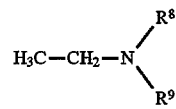

wherein $R^1$ is selected from the group consisting of a $C_1$–$C_5$ aliphatic group and $$H_3C-CH_2-N\overset{R^8}{\underset{R^9}{\diagup\!\!\!\diagdown}}$$

wherein
$R^8$ and $R^9$ are, independently, a $C_1$–$C_5$ alkyl group,
$R^2$ is a $C_1$–$C_{10}$ aliphatic group,
$R^3$ is a $C_1$–$C_{16}$ aliphatic group,
$R^4$ is selected from the group consisting of hydrogen and a $C_1$–$C_8$ aliphatic group,
$R^5$ is a $C_1$–$C_8$ aliphatic group,
$R^6$ is hydrogen or methyl,
$R^7$ is selected from the group consisting of hydrogen and an alkyl group having 1 to 4 carbon atoms; and (4) 3 to 40 weight percent based on the weight of ingredients (1), (2), (3) and (4) of a propellant selected from the group consisting of methane, ethane, propane, n-butane, isobutane, dimethyl ether and mixtures thereof.

3. A hair spray formulation according to claim 1, wherein the dicarboxylic acid comprises a dicarboxylic acid selected from the group consisting of terephthalic acid, phthalic acid, isophthalic acid, naphthalene-2,6-dicarboxylic acid, cyclohexanedicarboxylic acid, cyclohexanediacetic acid and mixtures thereof.

4. A hair spray formulation according to claim 3 wherein the dicarboxylic acid comprises isophthalic acid.

5. A hair spray formulation according to claim 1 wherein the diol comprises a mixture of 1,4-cyclohexanedimethanol and a diol selected from the group consisting of ethylene glycol, diethylene glycol, triethylene glycol and mixtures thereof.

6. A hair spray formulation according to claim 5 wherein the diol comprises a mixture of 1,4-cyclohexanedimethanol and diethylene glycol.

7. A hair spray formulation according to claim 1 wherein the difunctional sulfomonomer comprises a difunctional sulfomonomer selected from the group consisting of sulfophthalic acid, sulfoterephthalic acid, sulfoisophthalic acid, and 4-sulfonaphthalene-2,7-dicarboxylic acid.

8. A hair spray formulation according to claim 7 wherein the difunctional sulfomonomer comprises 5-sodiosulfoisophthalic acid.

9. A hair spray formulation according to claim 1 wherein the water-soluble polymer comprises a polymer selected from the group consisting of polyvinyl pyrrolidone, polyvinyl caprolactam, polyvinyl acetate, polyacrylates, methacrylates, and copolymers and terpolymers thereof.

10. A hair spray formulation according to claim 1 wherein the water-soluble polymer comprises a polymer selected from the group consisting of copolymers of polyvinylpyrrolidone and methylmethacrylate, copolymers of polyvinylpyrrolidone and vinyl acetate, copolymers of vinyl acetate and crotonic acid, terpolymers of polyvinyl alcohol/crotonic acid/vinyl neodecanoate, terpolymers of polyvinylpyrrolidone/ethylmethacrylate/methacrylic acid, and terpolymers of octylacrylamide/acrylate/butylaminoethyl methacrylate.

11. A hair spray formulation according to claim 2 wherein the propellant comprises dimethyl ether.

12. A hair spray formulation according to claim 2 wherein the propellant comprises a mixture containing 80 to 86 weight percent isobutane and 14 to 20 weight percent propane.

* * * * *